(12) United States Patent
McArthur et al.

(10) Patent No.: US 9,770,574 B2
(45) Date of Patent: Sep. 26, 2017

(54) TORQUE DEVICE AND SECUREMENT MECHANISM

(71) Applicant: Merit Medical Systems, Inc., South Jordan, UT (US)

(72) Inventors: Gregory R. McArthur, Sandy, UT (US); Timothy W. Clark, Philadelphia, PA (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/887,913

(22) Filed: Oct. 20, 2015

(65) Prior Publication Data

US 2016/0114139 A1    Apr. 28, 2016

Related U.S. Application Data

(60) Provisional application No. 62/067,208, filed on Oct. 22, 2014.

(51) Int. Cl.
*A61M 25/09* (2006.01)
*A61M 25/01* (2006.01)

(52) U.S. Cl.
CPC ...... *A61M 25/09041* (2013.01); *A61M 25/01* (2013.01); *A61M 2025/09116* (2013.01)

(58) Field of Classification Search
CPC ............ A61M 25/01; A61M 25/09041; A61M 2025/09116; F16G 11/04; F16G 11/048; F16G 11/10; F16G 11/101
USPC ....... 294/103.1; 24/115 G; 600/585; 604/528
See application file for complete search history.

(56) References Cited

U.S. PATENT DOCUMENTS

| | | |
|---|---|---|
| 3,215,027 A | 11/1965 | Modrey et al. |
| 3,452,740 A | 7/1969 | Muller |
| 4,102,478 A | 7/1978 | Samoilov |
| 4,796,626 A | 1/1989 | DeVries |
| 4,799,496 A | 1/1989 | Hargreaves et al. |
| 4,829,999 A | 5/1989 | Auth |
| 4,858,810 A | 8/1989 | Intlekofer et al. |
| 4,860,742 A | 8/1989 | Park et al. |
| 4,957,117 A | 9/1990 | Wysham |

(Continued)

FOREIGN PATENT DOCUMENTS

| | | |
|---|---|---|
| EP | 534747 | 3/1993 |
| EP | 2052756 | 4/2009 |
| WO | 0141860 | 6/2001 |

OTHER PUBLICATIONS

European Search Report dated May 29, 2009 for EP07753564.9.
(Continued)

*Primary Examiner* — Dean Kramer
(74) *Attorney, Agent, or Firm* — Stoel Rives LLP (57) ABSTRACT

A torque device for selectively securing, engaging, or gripping an elongate medical device is disclosed. The torque device can be configured to permit torquing of the elongate medical device by manipulation of the torque device. A securement mechanism for selectively securing, engaging, or gripping an elongate medical device is also disclosed. The securement mechanism may be adapted for use with the disclosed torque device, or the securement mechanism may also be adapted for use with other medical devices. For example, the securement mechanism may be adapted for use with a suture securement apparatus.

17 Claims, 6 Drawing Sheets

(56) References Cited

U.S. PATENT DOCUMENTS

| | | | |
|---|---|---|---|
| 4,973,329 | A | 11/1990 | Park et al. |
| 5,137,517 | A | 8/1992 | Loney et al. |
| 5,161,534 | A | 11/1992 | Berthiaume |
| 5,219,332 | A | 6/1993 | Nelson et al. |
| 5,312,338 | A | 5/1994 | Nelson et al. |
| 5,325,746 | A | 7/1994 | Anderson |
| 5,325,868 | A | 7/1994 | Kimmelstiel |
| 5,392,778 | A | 2/1995 | Horzewski |
| 5,423,331 | A | 6/1995 | Wysham |
| 5,634,475 | A | 6/1997 | Wolvek |
| 5,737,808 | A * | 4/1998 | Ikeda .................. F16G 11/10 24/115 G |
| 5,741,301 | A | 4/1998 | Pagedas |
| 5,800,447 | A | 9/1998 | Wenstrom, Jr. |
| 5,851,189 | A | 12/1998 | Forber |
| 5,919,161 | A | 7/1999 | Hill, III et al. |
| 5,971,994 | A | 10/1999 | Fritzsch |
| 5,987,344 | A | 11/1999 | West |
| 6,015,428 | A | 1/2000 | Pagedas |
| 6,030,349 | A | 2/2000 | Wilson et al. |
| 6,033,414 | A | 3/2000 | Tockman et al. |
| 6,059,484 | A | 5/2000 | Greive |
| 6,171,317 | B1 | 1/2001 | Jackson et al. |
| 6,371,940 | B1 | 4/2002 | Valencia et al. |
| 6,394,976 | B1 | 5/2002 | Winston et al. |
| 6,533,772 | B1 | 3/2003 | Sherts et al. |
| 6,626,917 | B1 | 9/2003 | Craig |
| 6,949,104 | B2 | 9/2005 | Griffis et al. |
| 7,011,635 | B1 | 3/2006 | Delay |
| 7,087,060 | B2 | 8/2006 | Clark |
| 7,144,378 | B2 | 12/2006 | Arnott |
| 7,416,556 | B2 | 8/2008 | Jackson |
| 7,785,348 | B2 | 8/2010 | Kuhns et al. |
| 7,831,297 | B2 * | 11/2010 | Opie ................ A61B 17/00008 600/434 |
| 7,850,712 | B2 | 12/2010 | Conlon et al. |
| 7,866,909 | B2 | 1/2011 | Denmark |
| 7,947,053 | B2 | 5/2011 | McKay et al. |
| 7,972,282 | B2 | 7/2011 | Clark et al. |
| 8,603,011 | B2 * | 12/2013 | Landowski ...... A61M 25/09041 600/585 |
| 2001/0031973 | A1 | 10/2001 | Nobles et al. |
| 2002/0026202 | A1 | 2/2002 | Honey et al. |
| 2003/0028203 | A1 | 2/2003 | Clark |
| 2003/0158581 | A1 | 8/2003 | Levinson |
| 2003/0225395 | A1 | 12/2003 | Griffis et al. |
| 2003/0229297 | A1 | 12/2003 | Christensen et al. |
| 2004/0067099 | A1 | 4/2004 | Warburton-Pitt |
| 2004/0215108 | A1 | 10/2004 | Windheuser |
| 2005/0070820 | A1 | 3/2005 | Boutillette et al. |
| 2005/0096566 | A1 | 5/2005 | Arnott |
| 2005/0235778 | A1 | 10/2005 | Murphy et al. |
| 2006/0030886 | A1 | 2/2006 | Clark |
| 2007/0106308 | A1 | 5/2007 | Onuki et al. |
| 2007/0112385 | A1 | 5/2007 | Conlon |
| 2007/0142786 | A1 | 6/2007 | Lampropoulos et al. |
| 2007/0219467 | A1 | 9/2007 | Clark et al. |
| 2008/0269785 | A1 | 10/2008 | Lampropoulos et al. |
| 2009/0234295 | A1 | 9/2009 | Lampropoulos et al. |
| 2010/0057110 | A1 | 3/2010 | Lampropoulos et al. |
| 2010/0100103 | A1 * | 4/2010 | Haskal ............ A61M 25/09041 606/108 |
| 2010/0191152 | A1 | 7/2010 | Boutillette et al. |
| 2013/0103001 | A1 | 4/2013 | BenMaamer et al. |

OTHER PUBLICATIONS

International Search Report and Written Opinion dated Jun. 25, 2009 for PCT/US2009/037168.
International Search Report and Written Opinion dated Dec. 14, 2007 for PCT/US2007/06945.
Notice of Allowance dated Jan. 9, 2015 for U.S. Appl. No. 12/202,073.
Notice of Allowance dated Jan. 10, 2006 for U.S. Appl. No. 10/198,161.
Notice of Allowance dated Feb. 25, 2015 for U.S. Appl. No. 12/404,227.
Notice of Allowance dated Apr. 28, 2011 for U.S. Appl. No. 11/688,766.
Notice of Allowance dated Oct. 20, 2011 for U.S. Appl. No. 12/106,204.
Notice of Allowance dated Nov. 21, 2014 for U.S. Appl. No. 12/202,073.
Office Action dated Feb. 6, 2007 for U.S. Appl. No. 11/244,168.
Office Action dated Feb. 7, 2005 for U.S. Appl. No. 10/198,161.
Office Action dated Feb. 15, 2012 for U.S. Appl. No. 12/404,227.
Office Action dated Mar. 16, 2010 for U.S. Appl. No. 11/688,766.
Office Action dated Mar. 21, 2011 for U.S. Appl. No. 12/106,204.
Office Action dated Apr. 6, 2005 for U.S. Appl. No. 10/198,161.
Office Action dated May 4, 2011 for U.S. Appl. No. 12/202,073.
Office Action dated May 20, 2014 for U.S. Appl. No. 12/404,227.
Office Action dated May 27, 2014 for U.S. Appl. No. 12/202,073.
Office Action dated Jun. 11, 2010 for U.S. Appl. No. 11/688,766.
Office Action dated Oct. 15, 2014 for U.S. Appl. No. 12/404,227.
Office Action dated Oct. 18, 2007 for U.S. Appl. No. 11/244,168.
Office Action dated Oct. 21, 2011 for U.S. Appl. No. 12/404,227.
Office Action dated Oct. 24, 2011 for U.S. Appl. No. 12/202,073.
Office Action dated Dec. 10, 2013 for U.S. Appl. No. 12/202,073.
Simons et al., 'The Woggle Technique: A New Method of Suture Closure of Hemodialysis Arteriovenous Grafts and Fistulae After Percutaneous Intervention', Journal of Vascular and Interventional Radiology 12(1):S30, 2001.
Vorwerk et al., 'A Simple Trick to Facilitate Bleeding Control After Percutaneous Hemodialysis Fistula and Graft Interventions', Cardiovascular Intervent Radiol 20(2)159-60, 1997.
Zaleski et al., 'Purse-String Sutures and Miniature Tourniquet to Achieve Immediate Hemostasis Grafts and Fistulas: A SimpleTrick with a Twist', Am. J. Roentgenol. 175(6):1643-5, 2000.
International Search Report and Written Opinion dated Jan. 13, 2016 for PCT/US2015/056407.

* cited by examiner

TORQUE DEVICE AND SECUREMENT MECHANISM

RELATED APPLICATIONS

This application claims priority to U.S. Provisional Application No. 62/067,208 titled "Torque Device and Securement Mechanism" filed on Oct. 22, 2014, which is hereby incorporated by reference in its entirety.

TECHNICAL FIELD

The present disclosure relates to torque devices and securement mechanisms configured to selectively secure, engage, or grip elongate medical devices to facilitate maneuvering of the elongate medical devices during medical procedures.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

DETAILED DESCRIPTION

The present disclosure is directed to a torque device that can be configured to selectively secure, engage, or grip an elongate medical device and facilitate displacement, such as translation or rotation, of the elongate medical device by manipulation of the torque device. According to one embodiment of the present disclosure, the torque device comprises a push-to-release configuration in which the device is automatically spring-biased to a position in which the torque device secures, engages, or grips the elongate medical device when an actuator of the torque device is unactuated or undepressed.

It will be appreciated by one of skill in the art having the benefit of this disclosure, that various features are sometimes grouped together in a single embodiment, figure, or description thereof for the purpose of streamlining the disclosure. Many of these features may be used alone and/or in combination with one another. It will further be appreciated by one of skill in the art having the benefit of this disclosure, that many of the features disclosed herein may be used in conjunction with other torque devices or torque device assemblies presently known or hereafter developed.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is a portion at the opposite end. For example, the proximal end of a torque device is defined as the end closest to the practitioner during utilization of the torque device. The distal end is the end opposite the proximal end, along the longitudinal direction of the torque device.

A variety of elongate medical devices may be utilized with the torque devices and/or the securement mechanisms of the present disclosure. Elongate medical devices as described herein include, but are not limited to, catheters, interventional tools, guidewires, sheaths, sutures, and tethers. Thus, specific disclosure below referencing specific elongate medical devices such as guidewires may analogously be applied to other elongate medical devices.

Guidewires or other interventional tools may be used for a variety of medical procedures. Such procedures include angioplasty, stenting, pacemaker insertion, electrophysiology studies, atherectomy, and thrombolysis and other coronary and peripheral endovascular procedures, and in endourology and therapeutic endoscopy of the gastrointestinal system. To position a guidewire at a desired location within a patient, a practitioner may navigate the guidewire through a patient's anatomy by manipulating the guidewire. Such manipulation can include advancing of the guidewire into the patient's vasculature or other portion of the patient's body while torquing the guidewire. Torquing the guidewire can allow the practitioner to change the spatial orientation of the end or the tip of the guidewire when negotiating turns and branches in the patient's vasculature or another relevant portion of the patient's anatomy.

Likewise, sutures may be used for a variety of medical procedures. Such procedures include the stitching of body tissues together after an injury or surgery. Multiple types of sutures have been developed and are adapted for a variety of tissues. For example, sutures are available in different materials, shapes, and/or sizes. Tethers may also be used for a variety of medical procedures. Such procedures include the identification or the labeling of corporeal structures.

Figure 1:
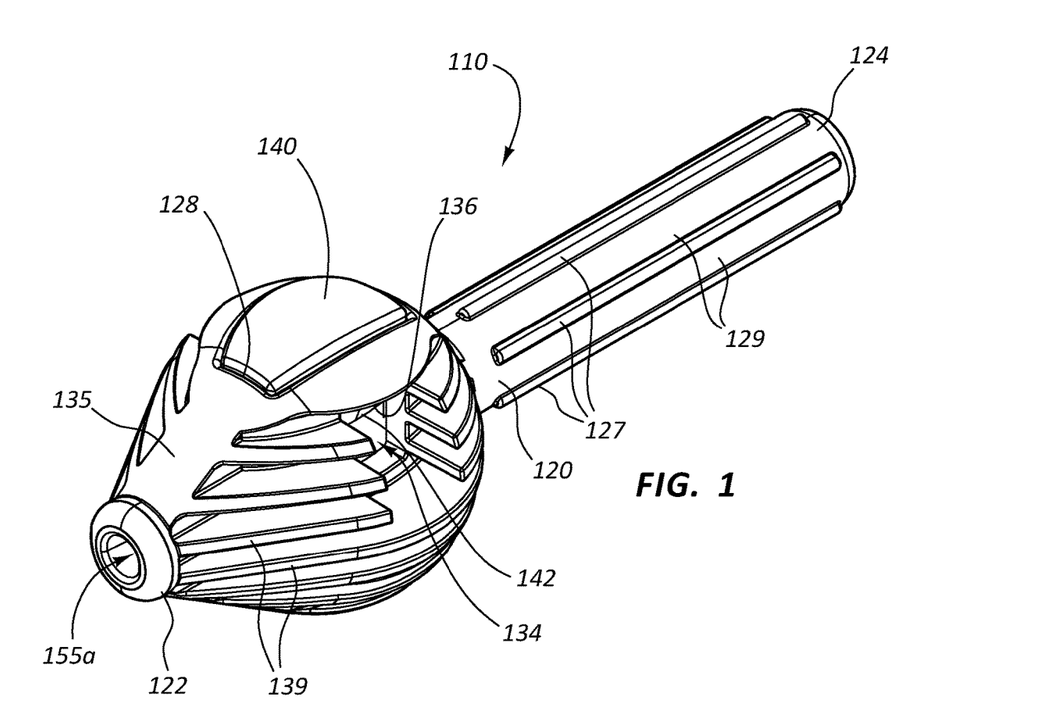
FIG. 1 is a perspective view of an embodiment of a torque device.

FIG. 1 is a perspective view of an embodiment of a torque device 110. In some embodiments, the torque device 110 can be configured to selectively secure, engage, or grip an elongate medical device to facilitate in the manipulation of the elongate medical device during a medical procedure. The torque device 110 can be configured to selectively secure, engage, or grip a guidewire, suture, tether, or other elongate medical device. For example, the torque device 110 may be configured to secure a tether to facilitate use of the tether in the identification of corporeal structures. In the illustrated embodiment, the torque device 110 comprises a housing 120 and an actuator 140.

The housing 120 can provide a base for the attachment of, or the coupling of, other components of the torque device 110. According to one embodiment of the present disclosure, the housing 120 is formed as a unitary body, as by injection molding of a polymeric material or similar material. In the illustrated embodiment, the housing 120 comprises a bulbous portion 135, a distal end portion 122, a proximal end portion 124, and a first channel 128 (the first channel 128 is described in more detail below). The bulbous portion 135 may allow or permit a practitioner to grasp the torque device 110 such that the practitioner may securely hold and manipulate the torque device 110 during a medical procedure. The substantially rounded or spherical shape of the bulbous portion 135 may provide for enhanced control or gripping of the torque device 110 by a practitioner in comparison to torque devices lacking such a bulbous portion. For example, the bulbous portion 135 may allow or permit the torque device 110 to remain gripped or secured by the practitioner even when the torque device 110 is rotated or moved from side to side during a medical procedure. In some embodiments, the distal end portion 122 may be integrally secured to the bulbous portion 135. In some other embodiments, the distal end portion 122 may be coupled to the bulbous portion 135. As depicted, the distal end portion 122 provides a second channel 155a that can allow for or permit introduction of an elongate medical device into the torque device 110.

In certain embodiments, the proximal end portion 124 may also be integrally secured to the bulbous portion 135 at a position substantially opposite the distal end portion 122. In certain other embodiments, the proximal end portion 124 may be coupled to the bulbous portion 135 at a position substantially opposite the distal end portion 122. As illustrated, the proximal end portion 124 defines a handle, which may also allow or permit a practitioner to grasp the torque device 110 such that the practitioner may hold and manipulate the torque device 110 during a medical procedure. Manipulation of the torque device 110 at the bulbous portion 135 may permit the practitioner to have enhanced or greater rotational control of the torque device 110, due at least in part to the greater diameter of the bulbous portion 135 in relation to the diameter of the proximal end portion 124. For example, with a larger diameter each degree of a turn is equal to a greater arc length, and thus there may be finer rotational control. In comparison, the practitioner may be able to more quickly or rapidly manipulate or rotate the torque device 110 when grasping the torque device 110 at the proximal end portion 124, as opposed to the bulbous portion 135, due at least in part to the smaller diameter of the proximal end portion 124 in relation to the bulbous portion 135. The second channel 155b (see FIG. 2) may also extend through at least a portion of the proximal end portion 124 such that introduction of an elongate medical device may also be allowed or permitted into the torque device 110 from a proximal end of the torque device 110.

As depicted on FIG. 1, the first channel 128 is defined by the bulbous portion 135. The first channel 128 can be configured to accommodate the actuator 140 and to allow for desired movement of the actuator 140 within the first channel 128. The first channel 128 may also provide a uniform, or substantially uniform, sliding surface that allows for or permits movement of the actuator 140 when the practitioner actuates or depresses the actuator 140 during operation of the torque device 110. In some embodiments, the actuator 140 may be biased toward an unactuated position. For example, the actuator 140 may be disposed or positioned in an unactuated position when the actuator 140 is not being actuated or depressed by a practitioner.

The bulbous portion 135, as illustrated, can further define one or more ridges 139 or a plurality of ridges 139. The one or more ridges 139 can be disposed parallel, or substantially parallel, in relation to each other. The bulbous portion 135 and/or the one or more ridges 139 may increase a surface friction or grippability of the torque device 110. For example, a practitioner's gloved hands and/or fingers may become slippery and/or wet during a medical procedure due to contact with one or more of a bodily fluid (e.g., blood) and/or a surgical fluid (e.g., saline). The bulbous portion 135 and/or the one or more ridges 139 may facilitate tactile gripping or securing of the torque device 110 by the practitioner even when his or her gloved hands and/or fingers are slippery or wet.

The proximal end portion 124, as depicted in FIG. 1, comprises ribs 127 and an outer grasping surface 129. The outer grasping surface 129 may be configured to enhance tactile grip. The outer grasping surface 129 is substantially cylindrical in overall shape, e.g., in transverse cross-section. Other shapes of the outer grasping surface 129 are also contemplated.

The ribs 127, as illustrated, comprise a plurality of longitudinally extending members which can provide an ergonomic grasping surface in connection with the outer grasping surface 129. The configuration of the ribs 127 can provide a relief surface on the exterior of the proximal end portion 124, which can facilitate grasping of the proximal end portion 124. The combination of the shape of the outer grasping surface 129 and the ribs 127 may facilitate manual grasping and manipulation of the torque device 110 by a practitioner.

In the illustrated embodiment, the actuator 140 is positioned within the first channel 128 of the housing 120. According to one embodiment, the actuator 140 is formed as a unitary body, as by injection molding of a polycarbonate material. The actuator 140 can allow the practitioner to engage or release an elongate medical device being utilized in connection with the torque device 110. When the actuator 140 is in an unactuated position, the torque device 110 can be positioned or repositioned along the length of an elongate medical device. When the actuator 140 is in an actuated position, the elongate medical device can be secured or engaged, allowing for gripping of the elongate medical device, advancing of the elongate medical device into the patient, and/or rotation of the elongate medical device to change a spatial orientation of a portion (e.g., an end or tip) of the elongate medical device.

The practitioner can actuate or depress the actuator 140 to release an elongate medical device allowing for movement or travel of the elongate medical device relative to the torque device 110. When the actuator 140 is unactuated or undepressed, the elongate medical device may be secured, minimizing movement or travel of the elongate medical device relative to the torque device 110. In the illustrated embodiment, the actuator 140 comprises a button. Other embodiments of the actuator 140 are also within the scope of this disclosure, including, but not limited to, adjusters, dials, knobs, switches, toggles, and triggers. Proper usage of the torque device 110 can be configured to be intuitive, decreasing or substantially decreasing the likelihood of misuse of the torque device 110 and/or inadvertent damage to an elongate medical device with which the torque device 110 may be utilized. For example, when the actuator 140 is actuated or depressed, an elongate medical device can be inserted through the torque device 110 from either the distal end portion 122 or the proximal end portion 124 of the torque device 110. Additionally, the configuration of the actuator 140 may minimize the ability of a practitioner to exert forces on the elongate medical device that exceed a desired amount of force that is automatically exerted on the elongate medical device when the actuator 140 is in the unactuated position.

When the actuator 140 is in the unactuated position, an elongate medical device being utilized with the torque device 110 may be engaged. In the illustrated embodiment, the actuator 140 comprises a catch 142 while the bulbous portion 135 of the housing 120 comprises a window 134 and a stop 136. The catch 142 may move within the window 134 during actuation or depression and unactuation or undepression of the actuator 140. The stop 136 can limit upward movement of the actuator 140 and retain the actuator 140 within the housing 120. The interaction between the stop 136 and the catch 142 can make it difficult and/or impractical for the practitioner to exert a higher degree of gripping force on the elongate medical device in a manner that may damage the elongate medical device. Damage to the elongate medical device may also be limited or reduced because the gripping force on the elongate medical device may be provided by a biasing member (discussed further below) rather than a force provided directly by a user, for example.

Figure 2:
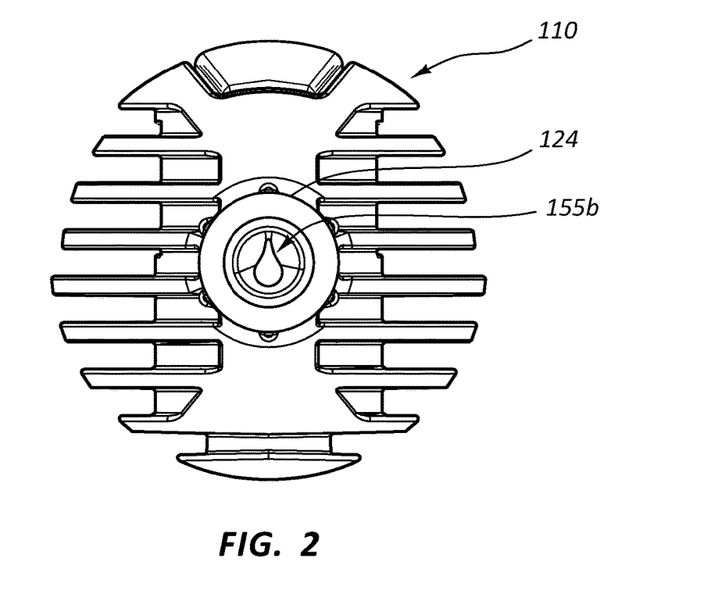
FIG. 2 is a proximal end view of the torque device of FIG. 1.

FIG. 2 is a proximal end view of the torque device 110 of FIG. 1. In the illustrated embodiment, a proximal portion of the second channel 155b that extends longitudinally along the length of at least a portion of the torque device 110 is illustrated. When a practitioner inserts an elongate medical device into the torque device 110 through the proximal end portion 124, the elongate medical device can be directed for insertion into the proximal portion of the second channel 155b.

Figure 3A:
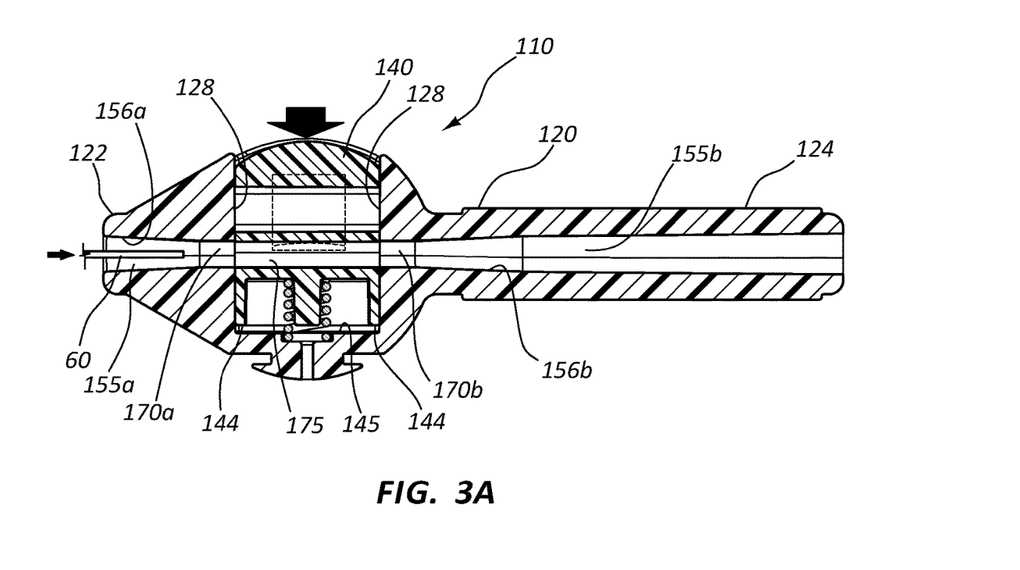
FIG. 3A is a cross-sectional side view of the torque device of FIG. 1, in a released configuration.
Figure 3B:
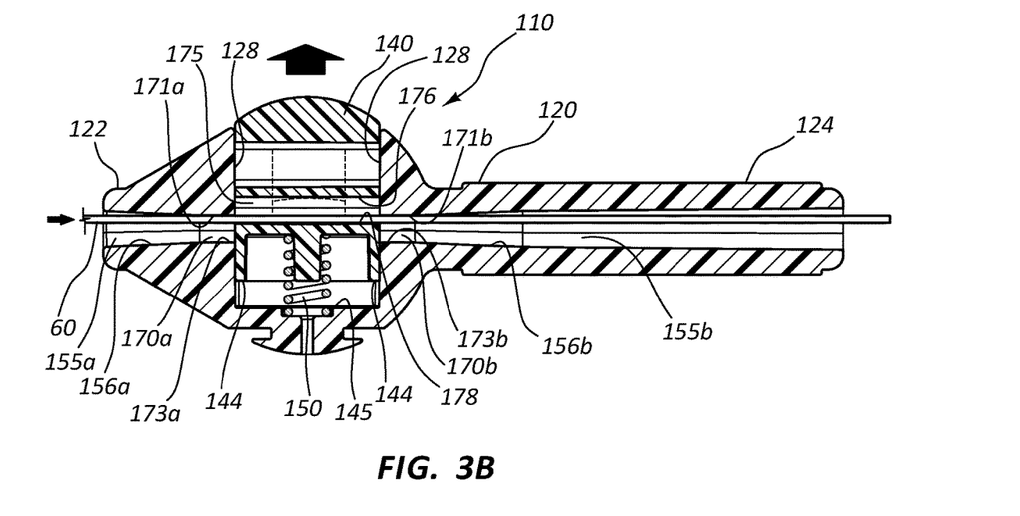
FIG. 3B is a cross-sectional side view of the torque device of FIG. 1, in a secured configuration.

FIG. 3A illustrates a cross-sectional side view of the torque device 110 of FIG. 1, in a released configuration. FIG. 3B illustrates a cross-sectional side view of the torque device 110 of FIG. 1, in a secured configuration. As depicted, the housing 120 can be elongated in a longitudinal direction and comprises a distal end portion 122 and a proximal end portion 124. A first lumen 170a, 170b (wherein the first lumen 170a is a portion of a lumen extending through at least a portion of the distal end portion 122 of the housing 120, and wherein the first lumen 170b is a portion of a lumen extending through at least a portion of the proximal end portion 124 of the housing 120) is provided, which permits passage of an elongate medical device 60 through at least a portion of the length of the housing 120. The actuator 140 defines a longitudinally extending second lumen 175. A combination of the first lumens 170a, 170b and the second lumen 175 can provide a luminal configuration or passageway that extends longitudinally through at least a portion of the torque device 110. Additionally, the first and second lumens 170a, 170b, 175 are dimensioned to receive one or more diameters, dimensions, sizes, and/or shapes of elongate medical devices.

As illustrated, a tapered surface 156a, which tapers to a wider opening, is disposed in the second channel 155a. The second channel 155a may be configured to facilitate insertion of an elongate medical device 60 into the torque device 110. For example, the tapered configuration of the tapered surface 156a may allow for a wider opening into which an end or a tip of an elongate medical device 60 can be inserted into the torque device 110. Once the elongate medical device 60 has been inserted into the second channel 155a, the tapered surface 156a can direct an end or a tip of the elongate medical device 60 to the narrower first lumen 170a of the torque device 110. The second channel 155b disposed or extending through at least a portion of the proximal end portion 124 may also comprise a tapered surface 156b that can facilitate insertion of an elongate medical device 60 into and/or through the proximal end portion 124 of the torque device 110 (i.e., in a manner similar to that described above regarding the second channel 155a and the tapered surface 156a).

With reference to FIG. 3A, the tapered surface 156a is provided in connection with the distal end portion 122, thus facilitating insertion of the elongate medical device 60 into the distal portion of the second channel 155a. As discussed above, the tapered configuration of the tapered surface 156a can allow for or permit a wider opening in which an end of the elongate medical device 60 can be inserted. Once the elongate medical device 60 has been inserted into the distal end portion 122, the tapered surface 156a may direct an end or a tip of the elongate medical device 60 to the relatively narrower first lumens 170a, 170b and second lumen 175.

The first channel 128 extends linearly and substantially perpendicularly to the longitudinal direction of the first and second lumens 170a, 170b, 175. The actuator 140 is disposed or mounted in the first channel 128 and is configured to move or slide substantially laterally in a linear direction that is substantially perpendicular to the longitudinal direction of elongation of the first and second lumens 170a, 170b, 175. When the actuator 140 is actuated or depressed (as indicated by the arrow), the first lumens 170a, 170b and the second lumen 175 may be substantially continuous through at least a portion of each of the housing 120 and the actuator 140. In other words, when the actuator 140 is actuated or depressed to align the second lumen 175 with the first lumens 170a, 170b, each of the first lumens 170a, 170b and the second lumen 175 comprise a sidewall that is substantially longitudinally continuous except for potential gaps between the actuator 140 and the housing 120 adjacent the proximal and distal ends of the second lumen 175. Thus, the first lumens 170a, 170b and the second lumen 175 can be substantially continuous from the distal end portion 122 of the housing 120, through the actuator 140, and to the proximal end portion 124 of the housing 120.

With continued reference to FIG. 3A, the actuator 140 is actuated or depressed such that the first lumens 170a, 170b and the second lumen 175 are longitudinally aligned to allow or permit passing of the elongate medical device 60 through the torque device 110. As illustrated, the actuator 140 comprises a stop surface 144 at or adjacent a bottom portion of the actuator 140. When the actuator 140 is fully depressed, the stop surface 144 may contact a floor 145 of the first channel 128. When the stop surface 144 abuts or is in contact with the floor 145 of the first channel 128, the second lumen 175 can be aligned with the first lumens 170a, 170b. Stated another way, to align the second lumen 175 and the first lumens 170a, 170b, and thus allow or permit passage of the elongate medical device 60 through each of the first lumens 170a, 170b and the second lumen 175 of the torque device 110, the practitioner can depress the actuator 140 until the practitioner can no longer displace the actuator 140 in a downward direction. This can provide for a simple, intuitive, and straightforward operation of the torque device 110.

With reference to FIG. 3B, the elongate medical device 60 is depicted as having been threaded along the entire length of the torque device 110. Further, the actuator 140 is unactuated or undepressed such that a biasing member 150, also referred to as a resilient biasing member, or a resilient member, has biased or displaced the actuator 140 to an unactuated or undepressed position (as indicated by the upward arrow). In some embodiments, such as in the illustrated embodiment, the biasing member 150 may comprise a spring, such as a coil spring. The biasing member 150 can be disposed within the housing 120 and/or be coupled to the actuator 140. The biasing member 150 may be configured to bias the actuator 140 toward the unactuated position from an actuated position. As depicted, the stop surface 144 of the actuator 140 is no longer in contact with the floor 145 of the first channel 128 and consequently the second lumen 175 is no longer aligned, or substantially aligned, with the first lumens 170a, 170b.

The second lumen 175 comprises an upper wall surface 176 and a lower wall surface 178. The upper wall surface 176 is continuous with the lower wall surface 178 through the second lumen 175. The first lumen 170a also comprises an upper wall surface 171a and a lower wall surface 173a. The upper wall surface 171a is continuous with the lower wall surface 173a through at least a portion of the distal end portion 122. Likewise, the first lumen 170b comprises an upper wall surface 171b and a lower wall surface 173b. The upper wall surface 171b is continuous with the lower wall surface 173b through at least a portion of the proximal end portion 124. When the actuator 140 is unactuated or undepressed, as depicted in FIG. 3B, the elongate medical device 60 can be cooperatively engaged between the lower wall surface 178 and the upper wall surfaces 171a, 171b. The cooperative engagement of the elongate medical device 60 between the lower wall surface 178 and the upper wall surfaces 171a, 171b may cooperatively secure, engage, or grip the elongate medical device 60 to maintain a position of the torque device 110 along the length of the elongate medical device 60.

With continued reference to FIG. 3B, the perpendicular movement of the actuator 140 relative to the housing 120 and to each of the first lumens 170a, 170b and the second lumen 175 can allow for closer tolerances between portions of each of the first lumens 170a, 170b and the second lumen 175 associated with the actuator 140 and the housing 120. As a result, bending of the elongate medical device 60 can be limited or minimized due to the interactions of the housing 120 and the actuator 140 when the elongate medical device 60 is in the engaged or secured configuration.

In the illustrated embodiment, the first lumens 170a, 170b and the second lumen 175 comprise a substantially continuous configuration. In other words, the actuator 140 and the second lumen 175 provide an increased area of contact between the actuator 140 and the elongate medical device 60 to minimize bending or kinking of the elongate medical device 60. The first lumens 170a, 170b may also provide an elongated contact area between the housing 120 and the elongate medical device 60. As compared with designs having only discrete points of contact, this arrangement can further limit or minimize bending or kinking of the elongate medical device 60. Additionally, contact between the elongate medical device 60, the second lumen 175, and the first lumens 170a, 170b can facilitate desired securing, engaging, or gripping of the elongate medical device 60. This, in turn, can result in the ability to use a biasing member 150 (e.g., a spring) having a lower spring force to provide the amount of friction or the level of securement that may be required to permit torquing of the elongate medical device 60 by torquing of the torque device 110. The lower spring force may result in greater ease of operation of the actuator 140, less manual fatigue of the practitioner, and less risk of damage to the elongate medical device 60 due to kinking, etc.

In the event that an elongate medical device 60 has not been inserted into the torque device 110 and wherein the actuator 140 is not actuated or depressed, the resulting lack of alignment between the second lumen 175 and the first lumens 170a, 170b can limit or prevent passage of the elongate medical device 60 through the torque device 110. In the event that a practitioner attempts to insert the elongate medical device 60 into the torque device 110 without first actuating or depressing the actuator 140, the intuitive nature and operability of the torque device 110 may result in depression of the actuator 140 by the practitioner when the practitioner recognizes that the elongate medical device 60 is encountering resistance. Stated another way, the design and operability of the torque device 110 can allow or permit practitioners and other medical professionals to load and operate the torque device 110 without specialized training and with decreased or minimized risk of damage to the elongate medical device 60.

Figure 4A:
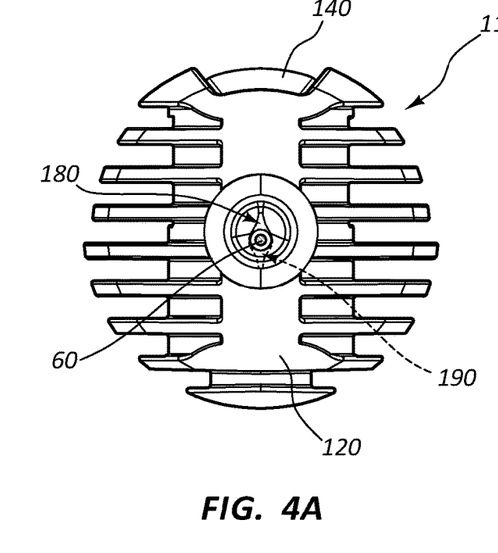
FIG. 4A is a distal end view of the torque device of FIG. 3A.
Figure 4B:
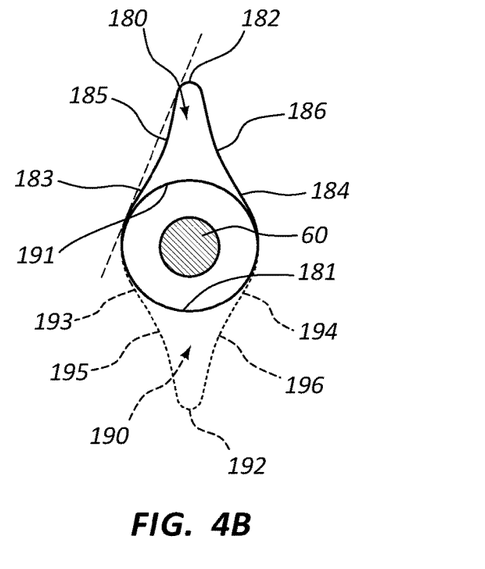
FIG. 4B is a detail view of a portion of the torque device of FIG. 4A.
Figure 5A:
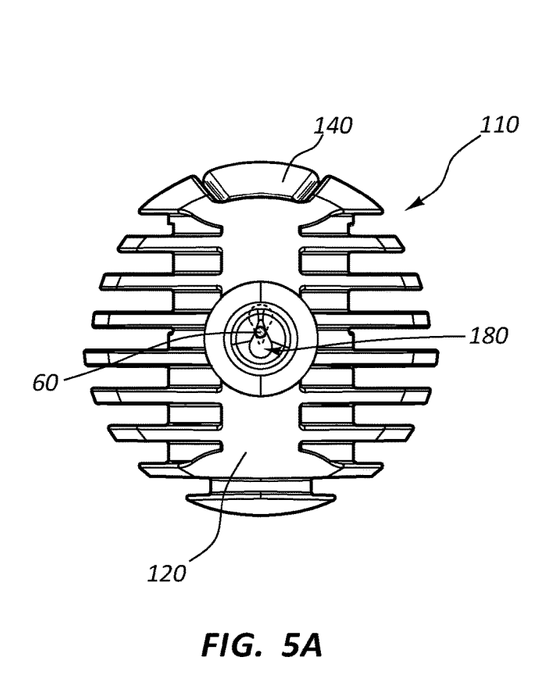
FIG. 5A is a distal end view of the torque device of FIG. 3B.

FIGS. 4A and 5A illustrate distal end views of the torque devices 110 of FIGS. 3A and 3B, respectively. In the illustrated embodiments, the housing 120 comprises a first opening 180. FIG. 4B, as depicted, illustrates a detail view of the first opening 180 of the housing 120 and the second opening 190 of the actuator 140 of the torque device 110 of FIG. 4A. With reference to FIG. 4B, the first opening 180 defines an arcuate (or rounded) first end portion 181 and a tapered (or pointed) second end portion 182. Further, a first lateral side 183 and a second lateral side 184 extend between the arcuate first end portion 181 and the tapered second end portion 182. Additionally, the first lateral side 183 comprises a first concave portion 185 and the second lateral side 184 comprises a second concave portion 186. The straight dashed line may act as a reference for observing the concave and/or arcuate displacement of the first concave portion 185 of the first lateral side 183. As depicted, the straight dashed line extends from a laterally disposed point along the arcuate first end portion 181 to a laterally disposed point along the tapered second end portion 182. Stated another way, the straight dashed line is tangent to both the arcuate first end portion 181 and an arc disposed at the tapered second end portion 182. In embodiments wherein the second end portion converges at a point, the straight dashed line may, for example, intersect that point. The concave portions 186, 195, 196 may also be similarly concavely or arcuately displaced. It can also be noted that the concavity of the first and second concave portions can be understood with respect to a reference point. For example, the first concave portion 185 of the first lateral side 183 may be considered concave from a reference point of the first opening 180, but the first concave portion 185 of the first lateral side 183 may be considered convex from a reference point of the surrounding housing 120.

With reference again to FIG. 4A, the actuator 140, which is slidably disposed within at least a portion of the housing 120, comprises the second opening 190. With reference again to FIG. 4B, the second opening 190 also defines an arcuate first end portion 191 and a tapered second end portion 192. Further, a first lateral side 193 and a second lateral side 194 extend between the arcuate first end portion 191 and the tapered second end portion 192. Additionally, the first lateral side 193 comprises a first concave portion 195 and the second lateral side 194 comprises a second concave portion 196. The first opening 180 and the second opening 190 may be configured for passage of an elongate medical device 60. For example, the first opening 180 and the second opening 190 may be dimensioned or sized for passage or reception of an elongate medical device 60.

With continued reference to FIG. 4B, the orientation of the arcuate first end portion 181 and the tapered second end portion 182 of the first opening 180 is substantially inverted in relation to the orientation of the arcuate first end portion 191 and the tapered second end portion 192 of the second opening 190. In some embodiments, the orientation of the first opening 180 in relation to the second opening 190 may be precisely inverted. In some other embodiments the orientation of the first opening 180 may be substantially inverted, or more or less than precisely inverted, in relation to the second opening 190.

The lateral dimensions of the arcuate first end portions 181, 191, or at least a portion of the arcuate first end portions 181, 191, are greater than the lateral dimensions of the tapered second end portions 182, 192, or at least a portion of the tapered second end portions 182, 192, respectively. For example, the arcuate first end portion 181 is generally wider than the tapered second end portion 182 and likewise the tapered second end portion 182 is generally narrower than the arcuate first end portion 181.

With reference to FIGS. 4A and 4B, when the actuator 140 is actuated or depressed, the larger cross-sectional areas of the arcuate first end portions 181, 191 of the first and second openings 180, 190 are aligned, or substantially aligned, allowing for clearance between the elongate medical device 60 and the sides of the first and second openings 180, 190. As a result, the elongate medical device 60 can be moved within each of the first and second openings 180, 190, allowing for or permitting threading of the elongate medical device 60 through the torque device 110 or repositioning of the torque device 110 along the length of the elongate medical device 60.

In various embodiments, when the actuator 140 is in an actuated position (i.e., a fully actuated position) the arcuate first end portions 181, 191 of the first and second openings 180, 190, respectively, are substantially aligned such that an elongate medical device 60 disposed or extending through the first and second openings 180, 190 is displaceable in relation to the torque device 110.

Figure 5B:
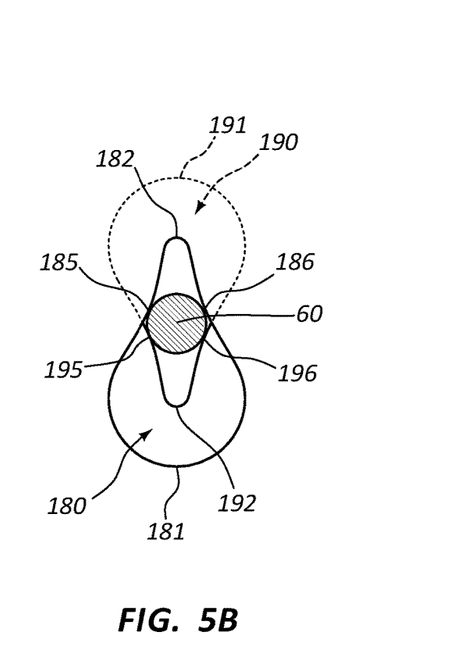
FIG. 5B is a detail view of a portion of the torque device of FIG. 5A.

With reference now to FIGS. 5A and 5B, when the actuator 140 is unactuated or undepressed, at least one or more of the first and second concave portions 185, 186, 195, 196 contact or engage the elongate medical device 60. Consequently, the elongate medical device 60 can be engaged between the first opening 180 and the second opening 190 with up to four points of contact between the first and second openings 180, 190 and an outer surface of at least a portion of the elongate medical device 60. Additionally, four elongated areas of contact may be provided at the interface of the second lumen 175 and the first lumens 170a, 170b (see FIG. 3B). Furthermore, contact can be provided along the length of the first lumens 170a, 170b and the second lumen 175 as depicted in FIG. 3B. As a result, improved or optimized securement of the elongate medical device 60 can be provided without exerting excessive forces on any one contact area along the length of the elongate medical device 60.

In certain embodiments, the first opening 180 can be a cross-section of at least a portion of the first lumens 170a, 170b extending through at least a portion of the housing 120. Likewise, the second opening 190 can be a cross-section of at least a portion of the second lumen 175 extending through at least a portion of the actuator 140 (see FIGS. 3A and 3B). Additionally, one or both of the first lumens 170a, 170b can be continuous, or substantially continuous, with the second lumen 175 when the torque device 110 is in the released configuration. In contrast, one or both of the first lumens 170a, 170b can be offset, or substantially offset, from the second lumen 175 when the torque device 110 is in the secured configuration. As discussed above, the actuator 140 and the second lumen 175 can provide an increased area of contact between the actuator 140 and the elongate medical device 60 to minimize bending or kinking of the elongate medical device 60. Likewise, the first lumens 170a, 170b can also provide an elongated contact area between the housing 120 and the elongate medical device 60.

The first and second concave portions 185, 186, 195, 196 allow for securement of a variety of diameters, dimensions, shapes, and/or sizes of elongate medical devices 60 in the secured configuration. For example, where a smaller elongate medical device 60 is utilized, the elongate medical device 60 may be engaged closer to the tapered second end portions 182, 192 of the first and second openings 180, 190 (see FIGS. 5A and 5B). Where a larger diameter elongate medical device 60 is utilized, the elongate medical device 60 may be engaged further from the tapered second end portions 182, 192 of the first and second openings 180, 190 (see FIG. 9). As a result, four elongated areas of contact and a similar overall contact area are provided by the first lumens 170a, 170b and the second lumen 175 notwithstanding the size of the elongated medical device 60 being utilized. According to one embodiment of the present disclosure, a single size of torque device 110 is configured to be utilized with guidewires in a range of between 0.010" and 0.038" in diameter. In another embodiment, a single size of lumen of torque device 110 is provided which can secure guidewires having a range of between 0.014" and 0.034" in diameter. In another embodiment, a single size of lumen of the torque device 110 is provided which can secure guidewires having a range of between 0.018" and 0.028" in diameter. A single size of torque device 110 configured to be utilized with guidewires in ranges of between additional diameters is also within the scope of this disclosure.

In certain embodiments, the torque device 110 is configured to transition between a released configuration (see FIG. 4A) and a secured configuration (see FIG. 5A). In the released configuration the elongate medical device 60 is displaceable or extendable through the first and second openings 180, 190 of the torque device 110. Stated another way, the elongate medical device 60 may be freely threaded through the first and second openings 180, 190 of the torque device 110 when the torque device 110 is in the released configuration. In the secured configuration, an elongate medical device 60 disposed or extending through the first and second openings 180, 190 of the torque device 110 can be secured, engaged, or gripped by at least the first and second openings 180, 190 of the torque device 110. Stated another way, the elongate medical device 60 may not be freely threaded through the first and second openings 180, 190 of the torque device 110 when the torque device 110 is in the secured configuration.

When the torque device 110 is in the released configuration, the arcuate first end portions 181, 191 of the first and second openings 180, 190, respectively, as depicted in FIG. 4B are aligned, or substantially aligned, such that an elongate medical device 60 is displaceable, extendable, or threadable through at least each of the first and second openings 180, 190. In contrast, when the torque device 110 is in the secured configuration, the arcuate first end portions 181, 191 of the first and second openings 180, 190, respectively, as depicted in FIG. 5B are misaligned, or substantially misaligned, such that a portion or portions of an elongate medical device 60 disposed through at least each of the first and second openings 180, 190 is/are secured by a cooperative engagement of the first and second openings 180, 190 with the portion, or portions, of the elongate medical device 60. In other words, an elongate medical device 60 may not be displaceable, extendable, or threadable through at least each of the first and second openings 180, 190 of the torque device 110 when the torque device 110 is in the secured configuration.

In various embodiments (see, e.g., FIGS. 5A and 5B), a portion of an elongate medical device 60 disposed through at least each of the first and second openings 180, 190 of the torque device 110 may be displaced by the housing 120 and/or the actuator 140 toward the tapered second end portions 182, 192 of the first and second openings 180, 190, respectively, when the torque device 110 is in the secured configuration. For example, a force or forces exerted by or via the housing 120 and/or the actuator 140 when the torque device 110 transitions from the released configuration to the secured configuration may move or transition at least a portion of an elongate medical device 60 disposed or extending through at least a portion of the housing 120 and/or the actuator 140 toward the tapered second end portions 182, 192 of the first and second openings 180, 190, respectively.

As illustrated in FIGS. 5A and 5B, each of the concave portions 185, 186, 195, 196 can engage a portion of the elongate medical device 60 disposed or extending through the first opening 180 and the second opening 190 when the torque device 110 is in the secured configuration. In some embodiments, at least three of the concave portions 185, 186, 195, 196 can engage a portion of an elongate medical device 60 disposed or extending through the first opening 180 and the second opening 190 when the torque device 110 is in the secured configuration. In some other embodiments, at least two of the concave portions 185, 186, 195, 196 can engage a portion of an elongate medical device 60 disposed or extending through the first opening 180 and the second opening 190 when the torque device 110 is in the secured configuration. In yet some other embodiments, at least one of the concave portions 185, 186, 195, 196 can engage a portion of an elongate medical device 60 disposed or extending through the first opening 180 and the second opening 190 when the torque device 110 is in the secured configuration.

The torque device 110 of the present disclosure may be configured for use with elongate medical devices 60 of various circumferences, diameters, dimensions, sizes, and/or shapes. As such, engagement between the concave portions 185, 186, 195, 196 of the first and second openings 180, 190 with an elongate medical device 60, or a portion of an elongate medical device 60, can depend on a cross-sectional dimension or size of the elongate medical device 60, or the portion of the elongate medical device 60, disposed or extending through the first and second openings 180, 190. For example, the elongate medical device 60, or a portion of the elongate medical device 60, may comprise a top portion, a bottom portion, a first lateral portion, and/or a second lateral portion. One or more of the concave portions 185, 186, 195, 196 of the first and second openings 180, 190 may be configured to engage or interact with at least one of the top portion, the bottom portion, the first lateral portion, and/or the second lateral portion of the elongate medical device 60, or the portion of the elongate medical device 60, disposed or extending through the first and second openings 180, 190.

When the actuator 140 is in the actuated position (see FIG. 4B), the arcuate first end portion 181 of the first opening 180 and the arcuate first end portion 191 of the second opening 190 may be substantially aligned such that an elongate medical device 60 is displaceable or extendable through the arcuate first end portions 181, 191. In contrast, when the actuator 140 is in the actuated position (see FIG. 5B) the arcuate first end portion 181 of the first opening 180 and the arcuate first end portion 191 of the second opening 190 may be substantially misaligned such that an elongate medical device 60 disposed or extending through the first opening 180 and the second opening 190 is secured by a cooperative engagement of the first opening 180 and the second opening 190 with at least a portion of the elongate medical device 60.

With continued reference to FIG. 5B, in some embodiments, the diameter of the tapered second end portion 182 of the first opening 180 may be about 0.008 inches. In such a configuration, an elongate medical device 60 (e.g., a guidewire) having a diameter of about 0.014 inches would not be displaced fully adjacent an end of the tapered second end portion 182 and would be engaged, at least in part, by portions of the first and second concave portions 185, 186 in the secured configuration. In another example, an elongate medical device 60 (e.g., a guidewire) having a diameter of about 0.038 inches would also not be displaced fully adjacent the end of the tapered second end portion 182 and would be engaged, at least in part, by the first and second concave portions 185, 186 in the secured configuration. Further, the 0.038 inch diameter elongate medical device 60 may be engaged by the first and second concave portions 185, 186 at a position more distal to the end of the tapered second end portion 182 than a position of engagement of the 0.014 inch diameter elongate medical device 60.

According to one embodiment of the present disclosure, the material properties of one or more components of the torque device 110 are designed to facilitate securement, engagement, or gripping of the elongate medical device 60. For example, according to one embodiment of the present disclosure, the housing 120, the actuator 140, and/or one or more portions of the first and second lumens 170*a*, 170*b*, 175 are composed of polypropylene, polyethylene, or acetyl resins such as DELRIN®, a combination of the aforementioned, or materials having similar shore properties. According to another embodiment of the present disclosure the material properties of the housing 120 and the actuator 140 are different from one another.

Figure 6:
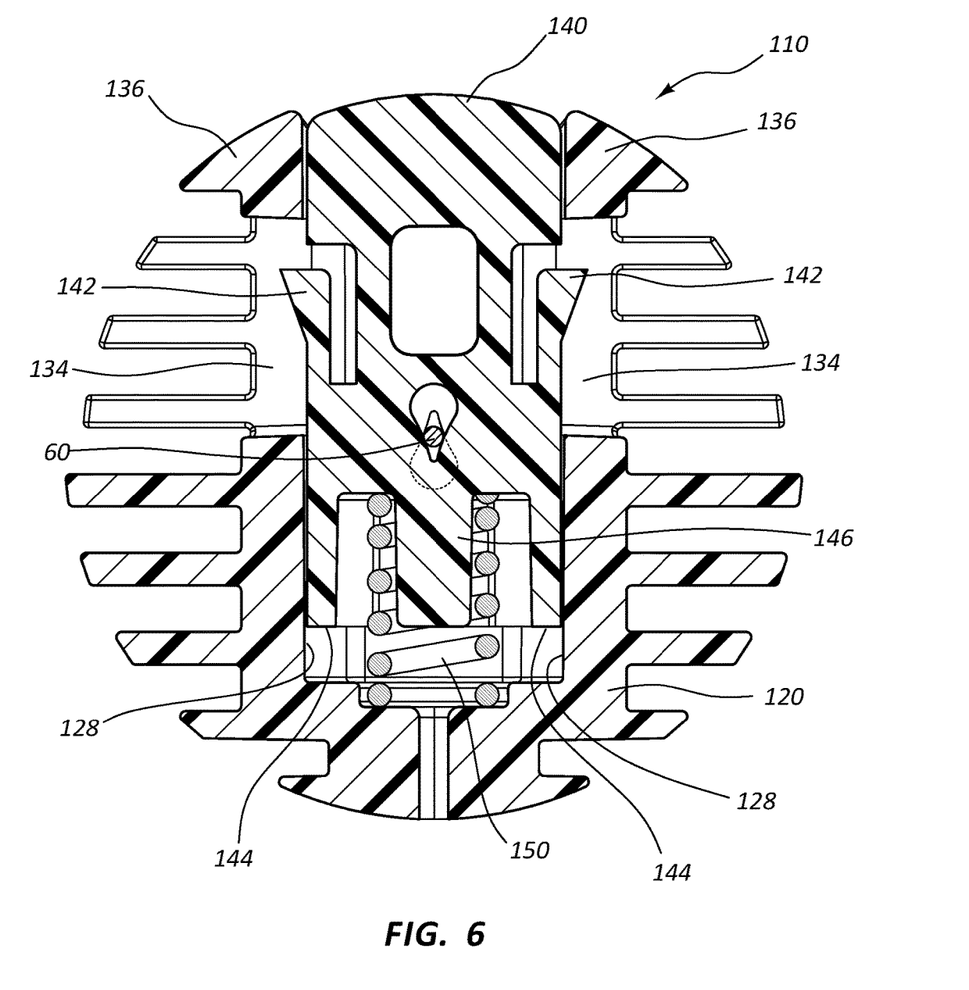
FIG. 6 is a cross-sectional view of the torque device of FIG. 5A.

FIG. 6 is a cross-sectional view of the torque device 110 of FIG. 5A. In the illustrated embodiment, the juxtaposition of the housing 120, the actuator 140, and the biasing member 150 is depicted. The housing 120 defines stops 136 and the actuator 140 defines catches 142, such that movement of the actuator 140 is limited by interference of at least one of the catches 142 with at least one of the stops 136. A resilient tang is one example of the catch 142. As will be appreciated by those skilled in the art, any suitable structures may be used to provide a stop and catch. In the exemplary embodiments, the housing 120 defines the windows 134, and the stops 136 are defined by a portion of the housing 120 adjacent the windows 134. Further, the catches 142 of the actuator 140 may be provided as resilient catches 142 that are received in the windows 134 and that interfere with the stops 136 of the housing 120 to retain the actuator 140 within the first channel 128.

As discussed above, the actuator 140 defines a stop surface 144. The stop surface 144 is positioned to limit or prevent movement or travel of the actuator 140 within the first channel 128 during actuation or depression of the actuator 140 beyond a point at which the arcuate first end portion 181 of the first opening 180 is longitudinally aligned with the arcuate first end portion 191 of the second opening 190 (see FIGS. 4A and 4B). In some embodiments, the forces exerted by the biasing member 150 on the actuator 140 are predetermined to limit or reduce the likelihood of damage to the elongate medical device 60. Optionally, the catches 142 and the windows 134 can be configured to limit upward movement or travel of the actuator 140 within the first channel 128 during unactuation or undepression of the actuator 140 to limit or reduce the likelihood of damage to the elongate medical device 60 due to shear forces applied to the elongate medical device 60 by the actuator 140 and the housing 120.

The torque device 110 further comprises the biasing member 150, which can be configured to bias the actuator 140 toward an unactuated position in which the second lumen is misaligned with the first lumens defined by the housing 120 (see FIG. 3B). As will be appreciated by those skilled in the art, the biasing member 150 may be any biasing and/or resilient body capable of providing resilient bias to the actuator 140. In the exemplary embodiments, the biasing member 150 is a coil spring. In the illustrated embodiment in which the biasing member 150 comprises a coil spring, the actuator 140 can further comprise a post 146 dimensioned to receive and support the biasing member 150.

The force exerted by a spring, such as a coil spring, is proportional to the magnitude of the displacement of the spring. In the torque device of the present disclosure, the first and second openings comprise first and second concave portions. As such, an elongate medical device engaged by cooperative engagement of the first and second openings is engaged at a position within the first and second openings nearer to the arcuate first end portions than an elongated medical device disposed through first and second openings lacking concave portions. This engagement corresponds to greater displacement of the spring, and thus greater resultant force, as compared to engagement nearer the end portions. For example, in embodiments wherein first and second openings comprise substantially straight first and second lateral sides (similar to the straight dashed line of FIG. 4B) an elongate medical device engaged by cooperative engagement of the first and second openings is engaged at a position within the first and second openings nearer to the tapered second end portions than an elongate medical device disposed through the first and second openings comprising concave portions. A shape of first and second lateral sides of the first and second openings (i.e., concave versus straight) affects or determines at what points the first and second openings contact or engage an outer surface of at least a portion of an elongate medical device disposed through the first and second openings. Consequently, in embodiments of the torque device comprising first and second concave portions a portion of the mechanical advantage of the spring can be preserved.

As discussed above, elongate medical devices having various diameters may be utilized with the torque devices of the present disclosure. Further, use of concave openings may facilitate use of a common torque device with multiple sizes of elongate medical devices. As noted above, the concave sides engage the medical device with less relative displacement than straight sided openings. Analogously, the difference in displacement between engaging large and small elongate medical devices is smaller when utilizing concave sides as compared to straight sides. This may, in turn, be configured to utilize a larger portion of the spring force (as compared to straight sides) even with small diameter medical devices. In other words, the difference in the engaging force supplied by the spring when gripping, for example, a small guidewire as compared to a large guidewire will be smaller than the same difference for straight sided openings.

Figure 7:
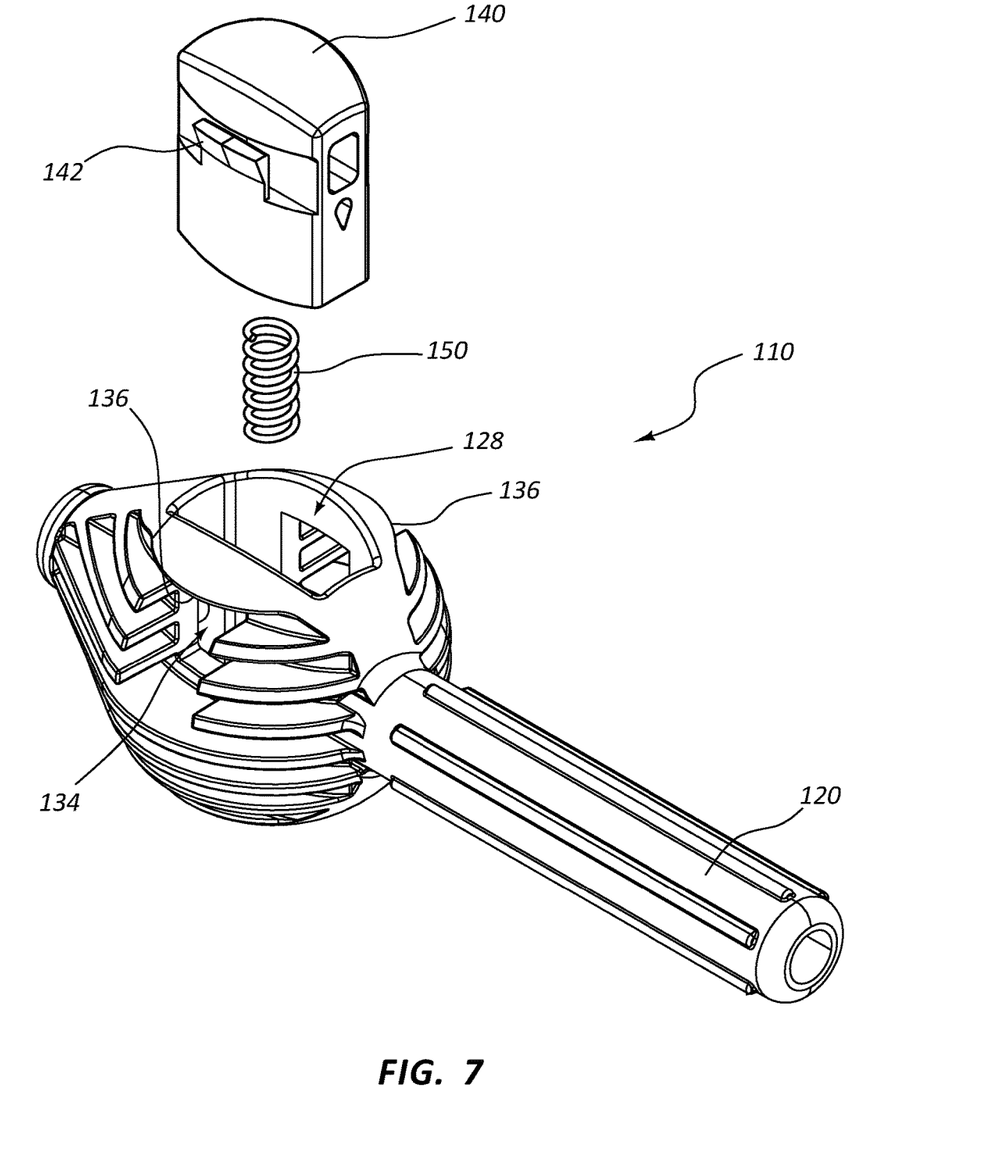
FIG. 7 is an exploded perspective view of the torque device of FIG. 1.

FIG. 7 is an exploded view of components of the torque device 110 of FIG. 1. The configuration of the torque device 110 can provide for simple and/or efficient assembly of the torque device 110. For example, the torque device 110 can be assembled by inverting the actuator 140, placing the biasing member 150 over the post 146 (see FIG. 6) of the actuator 140, and placing an inverted housing 120 over the actuator 140. The actuator 140 and the housing 120 may then be squeezed together until the resilient catches 142 deflect inwardly as they ride against the stops 136 of the housing 120, and then bias in an outward direction as they clear the stops 136 of the housing 120 and enter the windows 134 in the housing 120. Subsequent to insertion of the actuator 140 within the first channel 128, the torque device 110 may be a self-maintaining, integral assembly. In other words, the actuator 140 may not be ejected by the biasing member 150 if unactuated or undepressed, but instead the actuator 140 may be retained within the housing 120 due to interference of the catches 142 with the stops 136.

Figure 8:
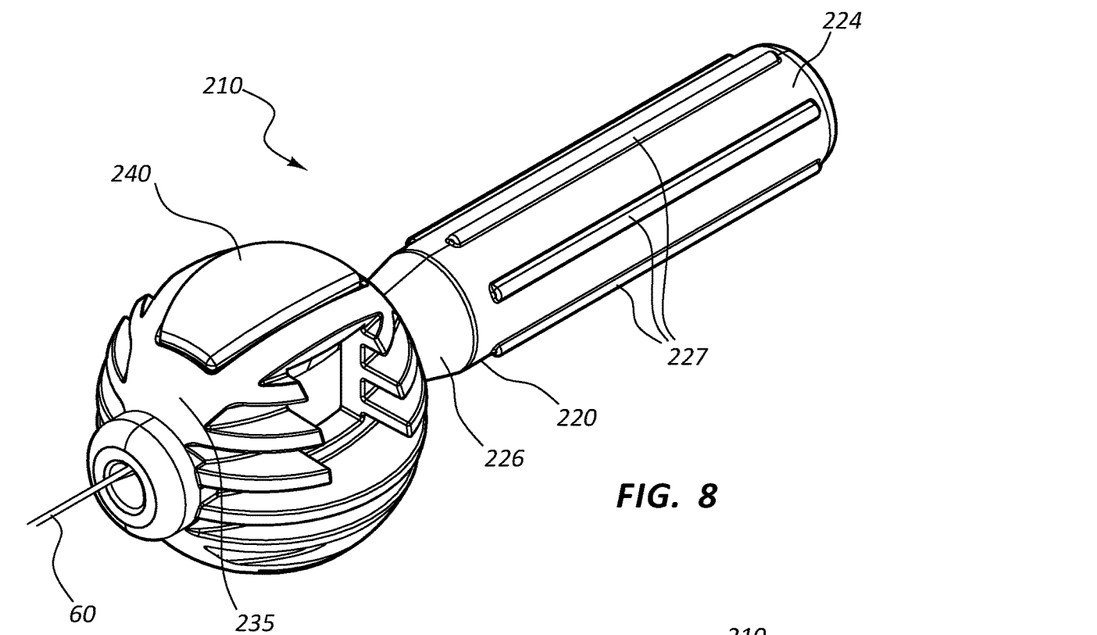
FIG. 8 is a perspective view of another embodiment of a torque device.

FIG. 8 illustrates a perspective view of another embodiment of a torque device that can, in certain respects, resemble components of the torque device described in connection with FIGS. 1-7. It will be appreciated that all the illustrated embodiments may have analogous features. Accordingly, like features are designated with like reference numerals, with the leading digits incremented to "2." For instance, the housing is designated "120" in FIGS. 1-7, and an analogous housing is designated as "220" in FIG. 8. Relevant disclosure set forth above regarding similarly identified features thus may not be repeated hereafter. Moreover, specific features of the torque device and related components shown in FIGS. 1-7 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the torque device of FIG. 8. Any suitable combination of the features, and variations of the same, described with respect to the torque device and components illustrated in FIGS. 1-7 can be employed with the torque device and components of FIG. 8, and vice versa. This pattern of disclosure applies equally to further embodiments depicted in subsequent figures and described hereafter.

In the illustrated embodiment of FIG. 8, the torque device 210 comprises a housing 220 and an actuator 240. The housing 220 can be a single molded piece having a proximal end portion 224 defining a handle and further comprising a plurality of ribs, or gripping surfaces, 227 and a tapered section 226. The tapered section 226 can be positioned at a portion of the proximal end portion 224 adjacent a bulbous portion 235. The tapered section 226 may facilitate grasping of the proximal end portion 224 when, for example, a practitioner is exerting a force on the elongate medical device 60. As such, the practitioner may be able to firmly grip the proximal end portion 224 when removing or withdrawing the elongated medical device 60 from a patient. In the illustrated embodiment, the housing 220 can be molded as a single member and the actuator 240 can be secured within the housing 220 by engagement of the actuator 240 with one or more internal components associated with the housing 220, as discussed above in reference to the torque device 110.

The illustrated bulbous portion 235 is more spherical than the bulbous portion 135 disclosed above (see FIG. 1). Other shapes and/or sizes of the bulbous portion 235 are also within the scope of this disclosure.

Figure 9:
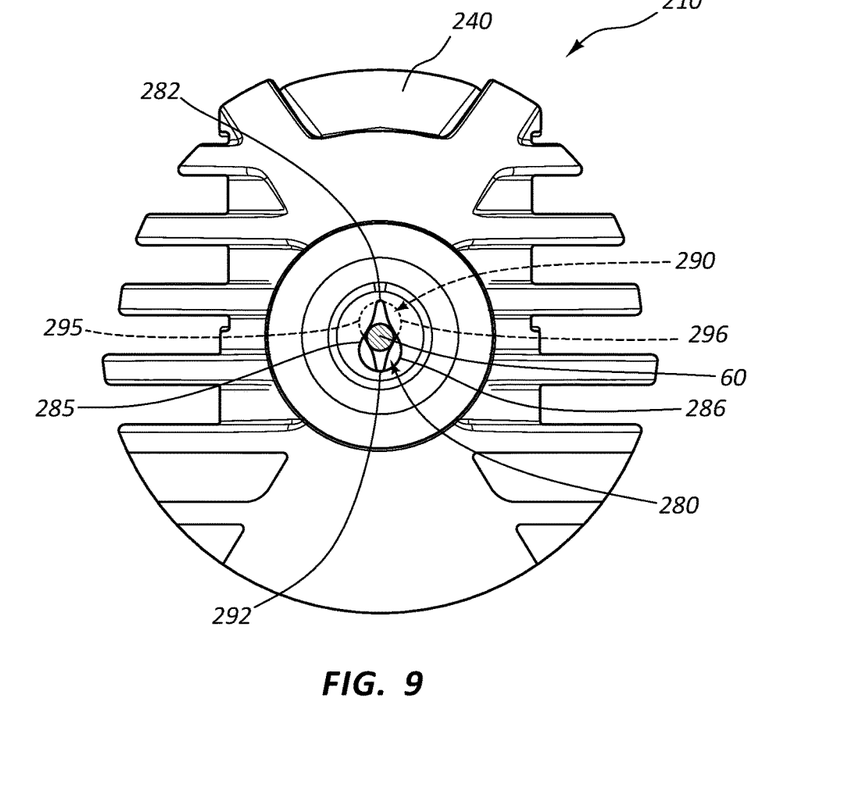
FIG. 9 is a distal end view of the torque device of FIG. 8.

FIG. 9 is a distal end view of the torque device 210 of FIG. 8. In the illustrated embodiment, the first and second openings 280, 290 are utilized to cooperatively engage a large diameter elongate medical device 60. Up to four concave portions 285, 286, 295, 296 contact or engage the elongate medical device 60. In this manner, the elongate medical device 60 is engaged between sides of the first and second openings 280, 290.

The shapes of the first and second openings 280, 290, as discussed in reference to the first and second openings 180, 190, allow for or permit engagement or securement of elongate medical devices 60 of a variety of diameters, dimensions, shapes, and/or sizes. For example, where a smaller diameter guidewire is utilized, the guidewire may be engaged closer to the tapered second end portions 182, 192 (see FIG. 4B). Where a larger diameter guidewire, such as the guidewire 60 depicted in FIG. 9, is utilized, the guidewire 60 may be engaged further from the tapered second end portions 282, 292.

A securement mechanism configured for engaging an elongate medical device comprising a first opening, similar to first opening 180, and a second opening, similar to second opening 190, may be adapted for use in a variety of other devices. For example, the securement mechanism may be adapted for use with a suture securement apparatus, such as the suture securement apparatus disclosed in U.S. Patent Application Publication No. 2009/0234295, titled SUTURE SECUREMENT APPARATUS, the entire contents of which are incorporated by reference herein.

As stated, the securement mechanism may comprise a first opening wherein the first opening defines an arcuate first end portion, similar to arcuate first end portion 181; a tapered second end portion, similar to tapered second end portion 182; a first lateral side, similar to first lateral side 183; and a second lateral side, similar to second lateral side 184, wherein the first and second lateral sides extend between the arcuate first end portion and the tapered second end portion. The first lateral side may comprise a first concave portion, similar to first concave portion 185, and the second lateral side may comprise a second concave portion, similar to second concave portion 186.

Additionally, as stated, the securement mechanism may further comprise a second opening, wherein the second opening is slidably disposed adjacent the first opening. The second opening may define an arcuate first end portion, similar to arcuate first end portion 191; a tapered second end portion, similar to tapered second end portion 192; a first lateral side, similar to first lateral side 193; and a second lateral side, similar to second lateral side 194, extending between the arcuate first end portion and the tapered second end portion. Further, the first lateral side may comprise a first concave portion, similar to first concave portion 195, and the second lateral side may comprise a second concave portion, similar to second concave portion 196. Further, an orientation of the arcuate first end portion and the tapered second end portion of the second opening may be inverted, or substantially inverted, in relation to the arcuate first end portion and the tapered second end portion of the first opening. As discussed above, the first opening and the second opening may be configured for passage of, or to receive, an elongate medical device.

In some embodiments, the securement mechanism can be configured to transition between a released configuration and a secured configuration. In the released configuration the arcuate first end portion of the first opening and the arcuate first end portion of the second opening may be aligned, or substantially aligned, such that an elongate medical device is displaceable or threadable through the arcuate first end portions. In the secured configuration, the arcuate first end portion of the first opening and the arcuate first end portion of the second opening may be misaligned, or substantially misaligned, such that an elongate medical device disposed or threaded through the first opening and the second opening may be engaged or secured by an interaction between or a cooperative engagement of at least a portion of the elongate medical device and the first and second openings.

In certain embodiments, when an elongate medical device is engaged by the securement mechanism at least one of the first concave portions and at least one of the second concave portions engage at least a portion of the elongate medical device disposed or extending through the first and second openings.

The securement mechanism may further comprise an actuator, wherein actuation or depression of the actuator displaces the second opening in a parallel plane in relation to the first opening. Additionally, the actuator may be biased such that when the actuator is in an unactuated position at least a portion of an elongate medical device disposed or threaded through the first and second openings is engaged by at least one of the first concave portions and at least one of the second concave portions.

In some embodiments, the first concave portion of the first opening may be substantially symmetrical to the second concave portion of the first opening, and/or the first concave portion of the second opening may be substantially symmetrical to the second concave portion of the second opening. Other relative shapes and/or sizes of the first and second concave portions are also contemplated. As discussed above, the elongate medical device for use in combination with the securement mechanism may be selected from at least one of a guidewire, suture, tether, or other elongate medical device.

An illustrative method of manipulating and/or securing an elongate medical device with a securement device may comprise, for example, disposing the elongate medical device within or through a portion of the securement device. In some instances, a practitioner may disposed the elongate medical device through each of a first opening and a second opening of the securement device. As described above, the first opening may be disposed adjacent to the second opening. The method of manipulating and/or securing the elongate medical device may further comprise displacing (i.e., slidably displacing) the second opening relative to the first opening such that at least one concave portion of at least one lateral side of the first opening and at least one concave portion of at least one lateral side of the second opening interact to engage and/or secure at least a portion of the elongate medical device.

In some embodiments, the method may further comprise use of an actuator to slidably displace the second opening in a parallel plane relative to the first opening. For example, the second opening may be disposed through at least a portion of the actuator, as discussed above. In certain embodiments, the method may further comprise grasping and rotating a portion of the securement device to rotate the elongate medical device. A practitioner may grasp a particular portion of the securement device depending on the nature of the intended rotation or other displacement. For example, a practitioner may grasp a bulbous portion, such as the bulbous portion described above, to manipulate or rotate the engaged and/or secured elongate medical device with a high degree of control. A practitioner may grasp another portion, such the proximal end portion discussed above to facilitate quicker rotation or manipulation of the secured device.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

The invention claimed is:

1. A torque device for securing an elongate medical device, the torque device comprising:
   a housing comprising a first opening, the first opening defining an arcuate first end portion and a tapered second end portion, and a first lateral side and a second lateral side extending between the first and second end portions, wherein each of the first lateral side and the second lateral side comprise a concave portion; and
   an actuator slidably disposed within at least a portion of the housing, the actuator comprising a second opening, the second opening defining an arcuate first end portion and a tapered second end portion, and a first lateral side and a second lateral side extending between the first and second end portions, wherein each of the first lateral side and the second lateral side comprise a concave portion, and
   wherein the first opening and the second opening are configured for passage of an elongate medical device.

2. The torque device of claim 1, wherein an orientation of the arcuate first end portion and the tapered second end portion of the first opening are substantially inverted in relation to the orientation of the arcuate first end portion and the tapered second end portion of the second opening.

3. The torque device of claim 1, wherein lateral dimensions of the arcuate first end portions are greater than lateral dimensions of the tapered second end portions.

4. The torque device of claim 1, wherein the torque device is configured to transition between a released configuration and a secured configuration, wherein the arcuate first end portions of the first and second openings are substantially aligned in the released configuration such that an elongate medical device is displaceable through the arcuate first end portions, and
   wherein the arcuate first end portions of the first and second openings are substantially misaligned in the secured configuration such that a portion of an elongate medical device disposed through the first opening and the second opening is secured by a cooperative engagement of the first opening and the second opening with the portion of the elongate medical device.

5. The torque device of claim 1, wherein a portion of an elongate medical device disposed through the first opening and the second opening is displaced by the housing and the actuator toward the tapered second end portions of the first and second openings when the torque device is in a secured configuration.

6. The torque device of claim 1, wherein at least two of the concave portions engage a portion of an elongate medical device disposed through the first opening and the second opening when the torque device is in a secured configuration.

7. The torque device of claim 1, wherein each of the concave portions engage a portion of an elongate medical device disposed through the first opening and the second opening when the torque device is in a secured configuration.

8. The torque device of claim 7, wherein positions of engagement between the concave portions with the portion of the elongate medical device depend on a cross-sectional size of the portion of the elongate medical device disposed through the first opening and the second opening.

9. The torque device of claim 1, further comprising:
a biasing member disposed within the housing and coupled to the actuator, the biasing member configured to bias the actuator toward an unactuated position from an actuated position, wherein the arcuate first end portion of the first opening and the arcuate first end portion of the second opening are substantially aligned when the actuator is in the actuated position such that an elongate medical device is displaceable through the arcuate first end portions, and
wherein the arcuate first end portion of the first opening and the arcuate first end portion of the second opening are substantially misaligned when the actuator is in the unactuated position such that an elongate medical device disposed through the first opening and the second opening is secured by a cooperative engagement of the first opening and the second opening with a portion of the elongate medical device.

10. The torque device claim 1, wherein when the actuator is in a fully actuated position the arcuate first end portions of the first and second openings are substantially aligned such that an elongate medical device extending through the first opening and the second opening is displaceable in relation to the torque device.

11. The torque device of claim 1, wherein the housing comprises a bulbous portion.

12. The torque device of claim 11, wherein the bulbous portion comprises a plurality of ridges.

13. The torque device of claim 12, wherein the plurality of ridges are disposed substantially parallel in relation to each other.

14. A securement mechanism for engaging an elongate medical device, the securement mechanism comprising:
a first opening defining an arcuate first end portion and a tapered second end portion, and a first lateral side and a second lateral side extending between the arcuate first end portion and the tapered second end portion, wherein the first lateral side comprises a first concave portion and wherein the second lateral side comprises a second concave portion; and
a second opening slidably disposed adjacent the first opening, the second opening defining an arcuate first end portion and a tapered second end portion, and a first lateral side and a second lateral side extending between the arcuate first end portion and the tapered second end portion, wherein the first lateral side comprises a first concave portion and wherein the second lateral side comprises a second concave portion, wherein an orientation of the arcuate first end portion and the tapered second end portion of the second opening is substantially inverted in relation to the arcuate first end portion and the tapered second end portion of the first opening, and
wherein the first opening and the second opening are configured to receive an elongate medical device.

15. The securement mechanism of claim 14, wherein the securement mechanism is configured to transition between a released configuration and a secured configuration, wherein the arcuate first end portion of the first opening and the arcuate first end portion of the second opening are substantially aligned in the released configuration such that an elongate medical device is displaceable through the arcuate first end portions, and
wherein the arcuate first end portion of the first opening and the arcuate first end portion of the second opening are substantially misaligned in the secured configuration such that an elongate medical device disposed through the first opening and the second opening is substantially engaged by an interaction between a portion of the elongate medical device and the first opening and the second opening.

16. The securement mechanism claim 14, wherein when an elongate medical device is engaged by the securement mechanism at least one of the first concave portions and at least one of the second concave portions engage a portion of the elongate medical device disposed through the first opening and the second opening.

17. The securement mechanism of claim 14, wherein the first concave portion of the first opening is substantially symmetrical to the second concave portion of the first opening, and
wherein the first concave portion of the second opening is substantially symmetrical to the second concave portion of the second opening.

* * * * *